(12) United States Patent
Viala et al.

(10) Patent No.: US 8,986,661 B2
(45) Date of Patent: Mar. 24, 2015

(54) SUN PROTECTION COMPOSITIONS

(75) Inventors: Sophie Viala, Cologne (DE); Sebastian Dorr, Dusseldorf (DE); Steffen Hofacker, Odenthal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/578,534

(22) PCT Filed: Mar. 1, 2011

(86) PCT No.: PCT/EP2011/053004
§ 371 (c)(1),
(2), (4) Date: Aug. 10, 2012

(87) PCT Pub. No.: WO2011/107462
PCT Pub. Date: Sep. 9, 2011

(65) Prior Publication Data
US 2012/0308496 A1 Dec. 6, 2012

(30) Foreign Application Priority Data
Mar. 5, 2010 (EP) .................................... 10002287

(51) Int. Cl.
*A61K 8/18* (2006.01)
*A61Q 17/04* (2006.01)
*A61K 8/40* (2006.01)
*A61K 8/87* (2006.01)

(52) U.S. Cl.
CPC . *A61Q 17/04* (2013.01); *A61K 8/40* (2013.01); *A61K 8/87* (2013.01)
USPC .......................................................... 424/59

(58) Field of Classification Search
None
See application file for complete search history.

(56) References Cited

U.S. PATENT DOCUMENTS

| 6,465,565 | B1 * | 10/2002 | Garcia et al. ................... 524/591 |
| 6,576,702 | B2 * | 6/2003 | Anderle et al. ................ 524/591 |
| 6,730,289 | B2 * | 5/2004 | Khoshdel ......................... 424/47 |
| 2002/0028875 | A1 * | 3/2002 | Anderle et al. ................ 524/591 |
| 2002/0155072 | A1 * | 10/2002 | Knuppel et al. ................. 424/59 |
| 2003/0044364 | A1 * | 3/2003 | Meyer et al. ..................... 424/59 |
| 2007/0254974 | A1 * | 11/2007 | Mager et al. ................... 521/172 |
| 2009/0041813 | A1 * | 2/2009 | Bouillo et al. ................. 424/401 |
| 2009/0081137 | A1 * | 3/2009 | Nguyen Kim et al. ......... 424/59 |
| 2009/0264587 | A1 * | 10/2009 | Blum et al. .................... 524/591 |
| 2011/0014139 | A1 | 1/2011 | Viala et al. |

FOREIGN PATENT DOCUMENTS

| DE | 10223693 A1 | 12/2003 |
| EP | 1214929 A2 | 6/2002 |
| EP | 2105124 A1 | 9/2009 |
| WO | 02053118 A2 | 7/2002 |
| WO | 2006/124250 A1 | 11/2006 |
| WO | WO 2006124250 A1 * | 11/2006 |
| WO | 2008006687 A1 | 1/2008 |
| WO | WO 2008006687 A1 * | 1/2008 |

OTHER PUBLICATIONS

International Search Report for PCT/EP2011/053004 Mailed June 4, 2012.

* cited by examiner

*Primary Examiner* — Robert A Wax
*Assistant Examiner* — Olga V Tcherkasskaya
(74) *Attorney, Agent, or Firm* — Miles and Stockbridge

(57) ABSTRACT

The invention relates to sun protection compositions for application on the skin, containing special polyurethanes and special sun filter combinations, and to the use of said polyurethanes and sun filter combinations for producing sun protection products.

19 Claims, No Drawings

SUN PROTECTION COMPOSITIONS

CROSS REFERENCE TO RELATED APPLICATIONS

This application is a §371 National Stage Application of PCT/EP2011/053004, filed Mar. 1, 2011, which claims priority to European Application No. 10002287.0, filed Mar. 5, 2010.

BACKGROUND OF THE INVENTION

1. Field of the Invention

The present invention relates to sun protection compositions for application to the skin, comprising special polyurethanes and special sun filter combinations, and also to the use of said polyurethanes and sun filter combinations for the preparation of sun protection products.

2. Description of Related Art

For years, tanned skin has been a synonym for attractive, healthy, sporty and successful people. In order to achieve this, people expose their skin to solar radiation. However, the solar rays have a harmful effect on the skin since they penetrate into the skin to varying depths depending on their wavelength. The shorter-wave radiation in the UVB region (wavelength: 280-320 nm) reaches the uppermost skin layer. Rays in the UVB region cause sunburn and are responsible for an increased risk of skin cancer. The longer-wave UVA rays (wavelength: 320-400 nm) penetrate into deeper skin layers. They lead to damage of the collagen and elastin fibres which are of essential importance for the structure and the strength of the skin. This leads, moreover, to premature skin ageing (formation of lines and wrinkles, irregular relief of the skin etc.). To protect the skin against solar radiations, photoprotective filter substances have been developed (UVA and UVB filters, contained in the form of positive lists such as Annex 7 of the Cosmetics Ordinance), which are used in cosmetic and dermatological compositions.

The sun protection products are often used on holiday or in leisure time on the beach or during sporting activities outside, where the body is in contact with water or perspiration. There is therefore the need to develop water-resistant and/or perspiration-resistant sun protection compositions. The production of such products is made possible through the use of selected technologies, such as, for example, water-in-oil (W/O) emulsions or through the use of hydrophobic film formers, such as, for example, alkylated polyvinylpyrrolidones.

The use of polyurethanes in sun protection compositions has already been described in the prior art. DE-A 10223693 describes the use of a polyurethanes which are formed from the polyaddition of 3-isocyanatomethyl 3,5,5-trimethylcyclohexyl-1-isocyanate and polyhydric alcohols, glycerides, hydroxy esters, silicone derivatives and/or amines. EP-A 1214929 describes the use of a film-forming, water-soluble or water-dispersible polyurethane for improving the water-resistance of a cosmetic or dermatological preparation comprising at least one UV filter. US-A 2003044364 describes the use of polyurethanes for improving the water resistance of sun protection formulations. EP-A 2 105 124 describes the use of special polyurethanes for improving application and also the skin feel when using the sun protection formulations.

However, there is furthermore the problem that prior art sun protection products, particularly in the case of a high sun protection factor (SPF), are difficult to spread on account of the often high required content of sun protection filter substances and, following application, leave behind an unpleasant waxy, sticky skin feel. Moreover, the content of certain sun protection filter substances is often restricted through legal provisions, meaning that in this regard limits are set in the selection of the composition to achieving a high SPF.

SUMMARY

The object of the present invention is therefore to develop a cosmetic or dermatological sun protection composition which have a high SPF and at the same time, in addition to excellent water resistance, has a good skin feel, i.e. a non-sticky and greasy skin feel. At the same time, other important properties, such as easy application, wear comfort, and no balling should also not be neglected.

Surprisingly, the object is achieved through the use of special polyurethanes or aqueous dispersions thereof, obtainable by reacting one or more water-insoluble, non-water-dispersible isocyanate-functional polyurethane prepolymers A) with one or more amino-functional compounds B), characterized in that the sun protection composition comprises a total of 16 to 35% by weight of sun protection filter substances, based on the total weight of the sun protection composition, and one of these sun protection filter substances is octocrylene which is present in an amount of from 4 to 12% by weight, based on the total weight of the sun protection composition.

DETAILED DESCRIPTION OF A PREFERRED EMBODIMENT

The present invention thus provides a sun protection composition comprising at least one polyurethane obtainable by reacting one or more water-insoluble, non-water-dispersible, isocyanate-functional polyurethane prepolymers A) with one or more amino-functional compounds B), which comprises a total of 16 to 35% by weight of sun protection filter substances, based on the total weight of the sun protection composition, and one of these sun protection filter substances is octocrylene which is present in an amount of from 4 to 12% by weight, based on the total weight of the sun protection composition.

Furthermore, the present invention provides a sun protection composition comprising at least one polyurethane obtainable by reacting one or more isocyanate-functional polyurethane prepolymers A) which have essentially neither ionic nor ionogenic groups, with one or more amino-functional compounds B), which comprises a total of 16 to 35% by weight of sun protection filter substances, based on the total weight of the sun protection composition, and one of these sun protection filter substances is octocrylene which is present in an amount of from 4 to 12% by weight, based on the total weight of the sun protection composition.

The composition according to the invention comprising the polyurethane and the specific amounts of the sun protection filter substances surprisingly has a considerably higher SPF than the mixture of the sun protection filter substances on their own, referred to hereinbelow as SPF-boosting effect. Such a significant increase in the sun protection factor (SPF) as a result of combining the sun protection filter substances with the polyurethanes was not to be expected by reference to the prior art and offers the advantage of achieving a high SPF by means of relatively small amounts of sun protection filter substances than would be required in sun protection compositions which comprise other sun protection filter substances, in particular no octocrylene, or no polyurethanes.

Within the context of the invention, the term "water-insoluble, non-water-dispersible polyurethane prepolymer" means in particular that the solubility in water of the prepolymer used according to the invention at 23° C. is less than 10 g/liter, more preferably less than 5 g/liter, and the prepolymer does not produce a sedimentation-stable dispersion in water, in particular deionized water, at 23°. In other words, the prepolymer settles out upon attempting to disperse it in water.

Preferably, the polyurethane prepolymer A) used according to the invention has terminal isocyanate groups, i.e. the isocyanate groups are at the chain ends of the prepolymer. All of the chain ends of a polymer particularly preferably have isocyanate groups.

Furthermore, the polyurethane prepolymer A) used according to the invention preferably has essentially neither ionic nor ionogenic (capable of forming ionic groups) groups, i.e. the content of ionic and ionogenic groups is expediently below 15 milliequivalents per 100 g of polyurethane prepolymer A), preferably below 5 milliequivalents, particularly preferably below 1 milliequivalent and very particularly preferably below 0.1 milliequivalent per 100 g of polyurethane prepolymer A).

The amino-functional compounds B) are preferably selected from primary and/or secondary amines and/or diamines. In particular, the amino-functional compounds B) include at least one diamine. The amino-functional compounds B) are preferably selected from amino-functional compounds B2), which have ionic or ionogenic group, and amino-functional compounds B1), which have no ionic or ionogenic group.

In a particularly preferred embodiment of the invention, the amino-functional compounds B) include at least one amino-functional compound B2) which has ionic and/or ionogenic (ion-forming) groups. The ionic and/or ionogenic group used is particularly preferably the sulphonate or the sulphonic acid group, yet more preferably the sodium sulphonate group.

In a further preferred embodiment of the invention, the amino-functional compounds B) include both amino-functional compounds B2) which have ionic and/or ionogenic group, and also amino-functional compounds B1) which have no ionic or ionogenic group.

Accordingly, polyurethanes within the context of the invention are polymeric compounds which have at least two, preferably at least three, repeat units containing urethane groups:

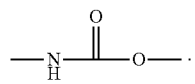

According to the invention, also included are those polyurethanes which, as a result of the preparation, also have repeat units containing urea groups:

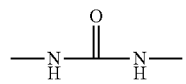

as are formed in particular in the reaction of the isocyanate-terminated prepolymers A) with the amino-functional compounds B).

The sun protection compositions according to the invention are preferably water-containing, i.e. aqueous, compositions in which the polyurethane is present in dispersed form, i.e. essentially not in dissolved form. In general, besides any other liquid media which may be present, such as, for example, solvents, water forms the main constituent (>50% by weight) of the dispersion media, based on the total amount of the liquid dispersion media in the cosmetic compositions according to the invention, and in some cases also forms the sole liquid dispersion medium.

The sun protection compositions according to the invention preferably have a content of volatile organic compounds (VOCs) of less than 80% by weight, more preferably of less than 55% by weight, even more preferably of less than 40% by weight, based on the sun protection composition.

The aqueous polyurethane dispersions used for the preparation of the sun protection compositions according to the invention preferably have a content of volatile organic compounds (VOCs) of less than 10% by weight, more preferably of less than 3% by weight, even more preferably of less than 1% by weight, based on the on aqueous polyurethane dispersion.

The content of volatile organic compounds (VOCs) is determined within the context of the present invention in particular by gas chromatographic analysis.

The non-water-soluble and non-water-dispersible, isocyanate-functional polyurethane prepolymers used according to the invention have essentially neither ionic nor ionogenic groups. The insolubility in water and/or lack of dispersibility in water refers to deionized water without the addition of surfactants. Within the context of the present invention this means that the proportion of ionic and/or ionogenic (ion-forming) groups, such as, in particular, anionic groups, such as carboxylate or sulphonate, or of cationic groups is less than 15 milliequivalents per 100 g of polyurethane prepolymer A), preferably less than 5 milliequivalents, particularly preferably less than 1 milliequivalent and very particularly preferably less than 0.1 milliequivalent per 100 g of polyurethane prepolymer A).

In the case of acidic ionic and/or ionogenic groups, the acid number of the prepolymer is expediently below 30 mg of KOH/g of prepolymer, preferably below 10 mg of KOH/g of prepolymer. The acid number indicates the mass of potassium hydroxide in mg which is required to neutralize 1 g of the sample under investigation (measurement in accordance with DIN EN ISO 211). The neutralized acids, i.e. the corresponding salts, naturally have no acid number or a reduced acid number. According to the invention, the acid number of the corresponding free acid is decisive here.

The prepolymers A) used for the preparation of the polyurethanes are preferably obtainable by reacting one or more polyols selected from the group which consists of polyether polyols, polycarbonate polyols, polyether polycarbonate polyols and/or polyester polyols, and polyisocyanates, as is explained in more detail below.

The polyurethanes present in the sun protection compositions according to the invention accordingly comprise, via the prepolymer A), preferably at least one sequence selected from the group which consists of: polyether, polycarbonate, polyether-polycarbonate and polyester sequences. According to the invention, this means in particular that the polyurethanes contain repeat units containing ether groups and/or carbonate groups or ester groups. The polyurethanes can contain, for example, exclusively polyether sequences or exclusively polycarbonate sequences or exclusively polyester sequences. However, they can also have both polyether and polycarbonate sequences, as are formed, for example, during the preparation of polycarbonate polyols using polyetherdiols, as is described in more detail below. In addition, they can have polyether-polycarbonate sequences which arise from the use of polyether-polycarbonate polyols, as described in more detail below.

Particularly preferred polyurethanes are obtained using polymeric polyether polyols and/or polymeric polycarbonate polyols and/or polyether-polycarbonate polyols or polyester polyols, each of which have number-average molecular weights of preferably about 400 to about 6000 g/mol (here and in the case of the molecular weight data below, determined by gel permeation chromatography relative to polystyrene standard in tetrahydrofuran at 23° C.). Their use during the preparation of the polyurethanes or polyurethane prepolymers leads, as a result of the reaction with polyisocyanates, to the formation of corresponding polyether and/or polycarbonate and/or polyether-polycarbonate sequences or polyester sequences in the polyurethanes with a corresponding molecular weight of these sequences. According to the invention, particular preference is given to polyurethanes which are obtained from polymeric polyetherdiols and/or polymeric polycarbonatediols and/or polyether-polycarbonate polyols or polyester polyols with a linear structure.

The polyurethanes according to the invention are preferably essentially linear molecules, but may also be branched, which is less preferred.

The number-average molecular weight of the polyurethanes preferably used according to the invention is, for example, about 1000 to 200 000, preferably from 5000 to 150 000.

The polyurethanes present in the sun protection compositions according to the invention are added to the specified compositions in particular in the form of aqueous dispersions.

Preferred polyurethanes or polyurethane dispersions to be used according to the invention are obtainable by
A) preparing isocyanate-functional prepolymers of
   A1) organic polyisocyanates,
   A2) polymeric polyols, preferably with number-average molecular weights of from 400 to 8000 g/mol (here and for the molecular weight data below, determined by gel permeation chromatography relative to polystyrene standard in tetrahydrofuran at 23° C.), more preferably 400 to 6000 g/mol and particularly preferably from 600 to 3000 g/mol, and OH functionalities of preferably 1.5 to 6, more preferably 1.8 to 3, particularly preferably from 1.9 to 2.1,
   A3) optionally hydroxy-functional compounds with molecular weights of preferably 62 to 399 g/mol, and
   A4) optionally nonionic hydrophilizing agents, and
B) then reacting some or all of their free NCO groups with one or more amino-functional compounds B), such as primary and/or secondary amines and/or diamines.

The polyurethanes used according to the invention are preferably dispersed in water before, during or after step B).

The reaction with a diamine or two or more diamines in step B) particularly preferably takes place with chain extension. In this connection, monofunctional amines can additionally be added as chain terminators to control the molecular weight.

As component B), in particular amines can be used which have no ionic or ionogenic, such as anionically hydrophilizing groups (component B1 below)) and it is possible to use amines which have ionic or ionogenic, such as, in particular, anionically hydrophilizing groups (component B2 below)).

Preferably, in step B) of the reaction of the prepolymer, a mixture of component B1) and component B2) is reacted. By using component B1) it is possible to build up a high molar mass without the viscosity of the previously prepared isocyanate-functional prepolymer increasing to a degree which would be an obstacle to processing. By using the combination of components B1) and B2) it is possible to achieve an optimum balance between hydrophilicity and chain length and thus establish a pleasant skin feel.

The polyurethanes used according to the invention preferably have anionic groups, preferably sulphonate groups. These anionic groups are introduced into the polyurethanes used according to the invention via the amine component B2) reacted in step B). The polyurethanes used according to the invention optionally additionally have nonionic components for hydrophilization. Exclusively sulphonate groups are particularly preferably present in the polyurethanes used according to the invention for the hydrophilization; these are introduced into the polyurethane via corresponding diamines as component B2).

In order to achieve a good sedimentation stability, the number-average particle size of the special polyurethane dispersions is preferably less than 750 nm, particularly preferably less than 500 nm, determined by means of laser correlation spectroscopy following dilution with deionized water (instrument: Malvern Zetasizer 1000, Malvern Inst. Limited).

The solids content of the polyurethane dispersions which is preferably used for preparing the sun protection composition of the invention is generally 10 to 70% by weight, preferably 30 to 65% by weight, particularly preferably 40 to 60% by weight. The solids contents are ascertained by heating a weighed sample at 125° C. to constant weight. At constant weight, the solid-body content is calculated by reweighing the sample.

Preferably, these polyurethane dispersions have less than 5% by weight, particularly preferably less than 0.2% by weight, based on the mass of the dispersions, of unbonded organic amines. The content in the sun protection compositions is correspondingly yet lower.

Suitable polyisocyanates of component A1) are in particular the aliphatic, aromatic or cycloaliphatic polyisocyanates with an NCO functionality of greater than or equal to 2 known per se to the person skilled in the art.

Examples of such suitable polyisocyanates are 1,4-butylene diisocyanate, 1,6-hexamethylene diisocyanate (HDI), isophorone diisocyanate (IPDI), 2,2,4- and/or 2,4,4-trimethylhexamethylene diisocyanate, the isomeric bis(4,4'-isocyanatocyclohexyl)methanes or mixtures thereof of any desired isomer content, 1,4-cyclohexylene diisocyanate, 4-isocyanatomethyl-1,8-octane diisocyanate (nonane triisocyanate), 1,4-phenylene diisocyanate, 2,4- and/or 2,6-tolylene diisocyanate, 1,5-naphthylene diisocyanate, 2,2'- and/or 2,4'- and/or 4,4'-diphenylmethane diisocyanate, 1,3- and/or 1,4-bis(2-isocyanatoprop-2-yl)benzene (TMXDI), 1,3-bis(isocyanatomethyl)benzene (XDI), and alkyl 2,6-diisocyanatohexanoates (lysine diisocyanates) with C1-C8-alkyl groups.

Besides the aforementioned polyisocyanates, it is also possible to use modified diisocyanates which have a functionality of ≥2 with uretdione, isocyanurate, urethane, allophanate, biuret, iminooxadiazinedione or oxadiazinetrione structure, and also mixtures of these proportionately.

They are preferably polyisocyanates or polyisocyanate mixtures of the type specified above with exclusively aliphatically or cycloaliphatically bonded isocyanate groups or mixtures of these and an average NCO functionality of the mixture of from 2 to 4, preferably 2 to 2.6 and particularly preferably 2 to 2.4, very particularly preferably 2.

Hexamethylene diisocyanate, isophorone diisocyanate or the isomeric bis(4,4'-isocyanatocyclohexyl)methanes, and mixtures of the aforementioned diisocyanates are particularly preferably used in A1).

In A2), polymeric polyols with a number-average molecular weight $M_n$ of preferably 400 to 8000 g/mol, more preferably from 400 to 6000 g/mol and particularly preferably from 600 to 3000 g/mol are used. These preferably have an OH functionality of from 1.5 to 6, particularly preferably from 1.8 to 3, very particularly preferably from 1.9 to 2.1.

The expression "polymeric" polyols means here in particular that the specified polyols have at least two, more preferably at least three, repeat units joined together.

Such polymeric polyols are the polyester polyols, polyacrylate polyols, polyurethane polyols, polycarbonate polyols, polyether polyols, polyester polyacrylate polyols, polyurethane polyacrylate polyols, polyurethane polyester polyols, polyurethane polyether polyols, polyurethane polycarbonate polyols and polyester polycarbonate polyols known per se in polyurethane coating technology. These can be used in A2) individually or in any desired mixtures with one another.

The preferably used polyester polyols are the polycondensates known per se of di- and optionally tri- and tetraols and di- and optionally tri- and tetracarboxylic acids or hydroxycarboxylic acids or lactones. Instead of the free polycarboxylic acids, it is also possible to use the corresponding polycarboxylic acid anhydrides or corresponding polycarboxylic acid esters of lower alcohols for the preparation of the polyesters.

Examples of suitable diols are ethylene glycol, butylene glycol, diethylene glycol, triethylene glycol, polyalkylene glycols, such as polyethylene glycol, also 1,2-propanediol, 1,3-propanediol, butanediol(1,3), butanediol(1,4), hexanediol(1,6) and isomers, neopentyl glycol or hydroxypivalic neopentyl glycol ester, where hexanediol(1,6) and isomers, butanediol(1,4), neopentyl glycol and hydroxypivalic neopentyl glycol ester are preferred. In addition, polyols such as trimethylolpropane, glycerol, erythritol, pentaerythritol, trimethylolbenzene or trihydroxyethyl isocyanurate can also be used.

Dicarboxylic acids which can be used are phthalic acid, isophthalic acid, terephthalic acid, tetrahydrophthalic acid, hexahydrophthalic acid, cyclohexanedicarboxylic acid, adipic acid, azelaic acid, sebacic acid, glutaric acid, tetrachlorophthalic acid, maleic acid, fumaric acid, itaconic acid, malonic acid, suberic acid, 2-methylsuccinic acid, 3,3-diethylglutaric acid and/or 2,2-dimethylsuccinic acid. The corresponding anhydrides may also be used as acid source.

If the average functionality of the polyol to be esterified is > than 2, monocarboxylic acids, such as benzoic acid and hexanecarboxylic acid, can additionally also be co-used.

Preferred acids are aliphatic or aromatic acids of the type specified above. Particular preference is given to adipic acid, isophthalic acid and phthalic acid.

Hydroxycarboxylic acids which can be co-used as reactants in the preparation of a polyester polyol with terminal hydroxyl groups are, for example, hydroxycaproic acid, hydroxybutyric acid, hydroxydecanoic acid, hydroxystearic acid and the like. Suitable lactones are caprolactone, butyrolactone and homologues. Preference is given to caprolactone.

According to the invention, particularly preferred components A2) for the preparation of the polyurethanes are polyester polyols with a number-average molecular weight of from 600 to 3000 g/mol, in particular aliphatic polyester polyols based on aliphatic carboxylic acids and aliphatic polyols, in particular based on adipic acid and aliphatic alcohols, such as hexanediol and/or neopentyl glycol.

Polycarbonates having hydroxyl groups, preferably polycarbonatediols, with number-average molecular weights $M_n$ of from preferably 400 to 8000 g/mol, preferably 600 to 3000 g/mol can likewise be used as component A2). These are obtainable by reacting carbonic acid derivatives, such as diphenyl carbonate, dimethyl carbonate or phosgene, with polyols, preferably diols.

Examples of such diols are ethylene glycol, 1,2- and 1,3-propanediol, 1,3- and 1,4-butanediol, 1,6-hexanediol, 1,8-octanediol, neopentyl glycol, 1,4-bishydroxymethylcyclohexane, 2-methyl-1,3-propanediol, 2,2,4-trimethylpentanediol-1,3, dipropylene glycol, polypropylene glycols, dibutylene glycol, polybutylene glycols, bisphenol A and lactone-modified diols of the type specified above.

Preferably, the diol component comprises 40 to 100% by weight of hexanediol, preference being given to 1,6-hexanediol and/or hexanediol derivatives. Such hexanediol derivatives are based on hexanediol and, besides terminal OH groups, have ester or ether groups. Such derivatives are obtainable by reacting hexanediol with excess caprolactone or by etherifying hexanediol with itself to give the di- or trihexylene glycol.

Instead of or in addition to the pure polycarbonatediols, it is also possible to use polyether-polycarbonatediols in A2). Polycarbonates having hydroxyl groups preferably have a linear structure.

Polyether polyols can likewise be used as component A2). For example, the polytetramethylene glycol polyethers known per se in polyurethane chemistry, as are obtainable through polymerization of tetrahydrofuran by means of cationic ring opening, are particularly suitable.

Likewise suitable polyether polyols are the addition products, known per se, of styrene oxide, ethylene oxide, propylene oxide, butylene oxide and/or epichlorohydrin onto di- or polyfunctional starter molecules. Thus, in particular polyalkylene glycols, such as polyethylene glycols, polypropylene glycols and/or polybutylene glycols, can be used, in particular those with the preferred molecular weights specified above.

Suitable starter molecules which can be used are all compounds known according to the prior art, such as, for example, water, butyl diglycol, glycerol, diethylene glycol, trimethylpropane, propylene glycol, sorbitol, ethylenediamine, triethanolamine 1,4-butanediol.

Particularly preferred components in A2) are polytetramethylene glycol polyethers and polycarbonate polyols and mixtures thereof and particularly preferably polytetramethylene glycol polyethers.

In preferred embodiments of the invention, component A2) is accordingly:
mixtures comprising at least one polyether polyol and at least one polycarbonate polyol,
mixtures comprising more than one polyether polyol, or a mixture of two or more polyether polyols with different molecular weights, which are in particular poly(tetramethylene glycol) polyether polyols (such as HO—(CH$_2$—CH$_2$—CH$_2$—CH$_2$—O)$_x$—H),
mixtures comprising more than one polyether polyol and at least one polycarbonate polyol, and also
particularly preferably polyester polyols with a number-average molecular weight of from 600 to 3000 g/mol, in particular aliphatic polyester polyols based on aliphatic carboxylic acids and aliphatic polyols, in particular based on adipic acid and aliphatic alcohols, such as hexanediol and/or neopentyl glycol,
where component A), according to the definition, has essentially neither ionic nor ionogenic groups.

As component A3), polyols, in particular nonpolymeric polyols, of the specified preferred molecular weight range from 66 to 399 mol/g with up to 20 carbon atoms, such as ethylene glycol, diethylene glycol, triethylene glycol, 1,2- propanediol, 1,3-propanediol, 1,4-butanediol, 1,3-butylene glycol, cyclohexanediol, 1,4-cyclohexanedimethanol, 1,6-hexanediol, neopentyl glycol, hydroquinone dihydroxy-ethyl ether, bisphenol A (2,2-bis(4-hydroxyphenyl)propane), hydrogenated bisphenol A (2,2-bis(4-hydroxycyclohexyl) propane), trimethylolpropane, trimethylolethane, glycerol, pentaerythritol and any desired mixtures thereof, can be used as desired. Also suitable are ester diols of the specified molecular weight range, such as α-hydroxybutyl ε-hydroxycaproic acid ester, ω-hydroxyhexyl γ-hydroxybutyric acid ester, adipic acid (β-hydroxyethyl) ester or terephthalic acid bis(β-hydroxyethyl) ester.

In addition, as component A3), it is also possible to use monofunctional isocyanate-reactive hydroxyl-group-containing compounds. Examples of such monofunctional compounds are ethanol, n-butanol, ethylene glycol monobutyl ether, diethylene glycol monomethyl ether, diethylene glycol monobutyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, tripropylene glycol monobutyl ether, 2-ethylhexanol, 1-octanol, 1-dodecanol, 1-hexadecanol.

In one preferred embodiment of the invention, the polyurethane used according to the invention comprises less than about 10% by weight of component A3), preferably less than 5% by weight of component A3), in each case based on the total mass of the polyurethane, yet more preferably component A3) is not used for the preparation of the polyurethane.

To prepare the polyurethanes used according to the invention, one or more in particular isocyanate-reactive nonionic hydrophilizing agents are optionally used as component A4). The hydrophilizing agents used as component A4) are in particular different from components A2) and A3).

Suitable nonionically hydrophilizing compounds as component A4) are, for example, polyoxyalkylene ethers which have isocyanate-reactive groups, such as hydroxy, amino or thiol groups. Preference is given to monohydroxy-functional polyalkylene oxide polyether alcohols having, on statistical average, 5 to 70, preferably 7 to 55, ethylene oxide units per molecule, as are accessible in a manner known per se by alkoxylation of suitable starter molecules (e.g. in Ullmanns Encyclopädie der technischen Chemie [Ullmanns encyclopaedia of industrial chemistry], 4th edition, Volume 19, Verlag Chemie, Weinheim pp. 31-38). These are either pure polyethylene oxide ethers or mixed polyalkylene oxide ethers, where they contain at least 30 mol %, preferably at least 40 mol %, ethylene oxide units, based on all of the alkylene oxide units present.

Particularly preferred nonionic compounds are monofunctional mixed polyalkylene oxide polyethers which have 40 to 100 mol % ethylene oxide units and 0 to 60 mol % propylene oxide units.

Suitable starter molecules for such nonionic hydrophilizing agents are in particular saturated monoalcohols, such as methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols or hydroxymethylcyclohexane, 3-ethyl-3-hydroxymethyloxetane or tetrahydrofurfuryl alcohol, diethylene glycol monoalkyl ethers, such as, for example, diethylene glycol monobutyl ether, unsaturated alcohols, such as allyl alcohol, 1,1-dimethylallyl alcohol or oleyl alcohol, aromatic alcohols, such as phenol, the isomeric cresols or methoxyphenols, araliphatic alcohols, such as benzyl alcohol, anisyl alcohol or cinnamyl alcohol, secondary monoamines, such as dimethylamine, diethylamine, dipropylamine, diisopropylamine, dibutylamine, bis(2-ethylhexyl)amine, N-methyl- and N-ethylcyclohexylamine or dicyclohexylamine, and also heterocyclic secondary amines, such as morpholine, pyrrolidine, piperidine or 1H-pyrazole. Preferred starter molecules are saturated monoalcohols of the type specified above. Particular preference is given to using diethylene glycol monobutyl ether or n-butanol as starter molecules.

Alkylene oxides suitable for the alkoxylation reaction are in particular ethylene oxide and propylene oxide, which can be used in the alkoxylation reaction in any desired order or else in a mixture. Component B) is preferably selected from primary or secondary amine and/or diamines. It includes in particular diamines. As component B) it is possible to use in particular amines which have no ionic or ionogenic, such as anionically hydrophilizing groups (component B1) below), and it is possible to use amines which have ionic or ionogenic, such as, in particular, anionically hydrophilizing groups (component B2) below). Preferably, in step B) of the reaction of the prepolymer, a mixture of component B1) and of component B2) is reacted.

For example, organic di- or polyamines, such as, for example, 1,2-ethylenediamine, 1,2- and 1,3-diaminopropane, 1,4-diaminobutane, 1,6-diaminohexane, isophoronediamine, isomer mixture of 2,2,4- and 2,4,4-trimethylhexamethylenediamine, 2-methylpentamethylenediamine, diethylenetriamine, 4,4-diaminodicyclohexylmethane, hydrazine hydrate, and/or dimethylethylenediamine, can be used as component B1).

Moreover, compounds which, besides a primary amino group, also have secondary amino groups or, besides an amino group (primary or secondary), also have OH groups, can also be used as component B1). Examples thereof are primary/secondary amines, such as diethanolamine, 3-amino-1-methylaminopropane, 3-amino-1-ethylaminopropane, 3-amino-1-cyclohexylaminopropane, 3-amino-1-methylaminobutane, alkanolamines, such as N-aminoethylethanolamine, ethanolamine, 3-aminopropanol, neopentanolamine.

In addition, monofunctional isocyanate-reactive amine compounds can also be used as component B1), such as, for example, methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl (methyl)aminopropylamine, morpholine, piperidine, and suitable substituted derivatives thereof, amidoamines of diprimary amines and monocarboxylic acids, monoketime of diprimary amines, primary/tertiary amines, such as N,N-dimethylaminopropylamine. As component B1), preference is given to using 1,2-ethylenediamine, bis(4-aminocyclohexyl) methane, 1,4-diaminobutane, isophoronediamine, ethanolamine, diethanolamine and diethylenetriamine.

Component B) particularly preferably includes at least one component B2). Suitable anionically hydrophilizing compounds as component B2) preferably contain a sulphonic acid or sulphonate group, particularly preferably a sodium sulphonate group. Suitable anionically hydrophilizing compounds as component B2) are, in particular, the alkali metal salts of mono- and diaminosulphonic acids. Examples of such anionic hydrophilizing agents are salts of 2-(2-aminoethylamino)ethanesulphonic acid, ethylenediaminepropyl- or -butylsulphonic acid, 1,2- or 1,3-propylenediamine-R-ethylsulphonic acid or taurine. Furthermore, the salt of cyclohexylaminopropanesulphonic acid (CAPS) from WO-A 01/88006 can be used as anionic hydrophilizing agent.

Particularly preferred anionic hydrophilizing agents B2) are those which contain sulphonate groups as ionic groups and two amino groups, such as the salts of 2-(2-aminoethylamino)ethylsulphonic acid and 1,3-propylenediamine-β-ethylsulphonic acid. The polyurethanes used according to the invention particularly preferably comprising at least one sulphonate group.

Optionally, the anionic group in component B2) may also be a carboxylate or carboxylic acid group. Component B2) is then preferably selected from diaminocarboxylic acids. However, this embodiment is less preferred since carboxylic-acid-based components B2) have to be used in higher concentrations.

For the hydrophilization, it is also possible to use mixtures of anionic hydrophilizing agents B2) and nonionic hydrophilizing agents A4).

In a preferred embodiment for the preparation of the special polyurethane dispersions, components A1) to A4) and B1) to B2) are used in the following amounts, the individual amounts always adding up to 100% by weight:
5 to 40% by weight of component A1),
55 to 90% by weight of A2),
0.5 to 20% by weight sum of components A3) and/or B1),
0.1 to 25% by weight sum of components A4) and/or B2),
where, based on the total amounts of components A1) to A4) and B1) to B2), particularly preferably 0.1 to 5% by weight of anionic or potentially anionic hydrophilizing agents B2) are used.

In a particularly preferred embodiment for the preparation of the special polyurethane dispersions, components A1) to A4) and B1) to B2) are used in the following amounts, the individual amounts always adding up to 100% by weight:
5 to 35% by weight of component A1),
60 to 90% by weight of A2),
0.5 to 15% by weight sum of components A3) and/or B1),
0.1 to 15% by weight sum of components A4) and/or B2),
where, based on the total amounts of components A1) to A4) and B1) to B2), particularly preferably 0.2 to 4% by weight of anionic or potentially anionic hydrophilizing agents B2) are used.

In a very particularly preferred embodiment for the preparation of the special polyurethane dispersions, components A1) to A4) and B1) to B2) are used in the following amounts, the individual amounts always adding up to 100% by weight:
10 to 30% by weight of component A1),
65 to 85% by weight of A2),
0.5 to 14% by weight sum of components A3 and/or B1),
0.1 to 13.5% by weight sum of components A4) and/or B2),
where, based on the total amounts of components A1) to A4) and B1) to B2, particularly preferably 0.5 to 3.0% by weight of anionic or potentially anionic hydrophilizing agents from B2) are used.

The preparation of the polyurethane dispersions can be carried out in one or more stage(s) in homogeneous phase or, in the case of multistage reaction, sometimes in disperse phase. Following complete or partial polyaddition from A1) to A4), a dispersion, emulsification or dissolution step preferably takes place. Afterwards, a further polyaddition or modification optionally takes place in the disperse phase.

In this connection, all of the methods known from the prior art, such as, for example, prepolymer mixing process, acetone process or melt dispersion process, can be used. Preference is given to using the acetone process.

For the preparation in accordance with the acetone process, constituents A2) to A4) and the polyisocyanate component A1) for the preparation of an isocyanate-functional polyurethane prepolymer are usually initially introduced in their entirety or in part and optionally diluted with a solvent which is miscible with water but inert towards isocyanate groups, and heated to temperatures in the range from 50 to 120° C. To increase the rate of the isocyanate addition reaction, the catalysts known in polyurethane chemistry can be used.

Suitable solvents are the customary aliphatic, keto-functional solvents such as acetone, 2-butanone, which can be added not only at the start of the preparation, but optionally in parts also later on. Preference is given to acetone and 2-butanone, and particular preference is given to acetone. The addition of other solvents without isocyanate-reactive groups is also possible, but not preferred.

Any constituents of A1) to A4) not added at the start of the reaction are then metered in.

During the preparation of the polyurethane prepolymer from A1) to A4), the quantitative ratio of isocyanate groups to isocyanate-reactive groups is generally 1.05 to 3.5, preferably 1.1 to 3.0, particularly preferably 1.1 to 2.5.

The reaction of components A1) to A4) to give the prepolymer takes place partially or completely, but preferably completely. Polyurethane prepolymers which contain free isocyanate groups are thus obtained without a diluent or in solution.

In the neutralization step for the partial or complete conversion of potentially anionic groups to anionic groups, bases such as tertiary amines, e.g. trialkylamines having 1 to 12, preferably 1 to 6, carbon atoms, particularly preferably 2 to 3 carbon atoms in each alkyl radical or very particularly preferably alkali metal bases such as the corresponding hydroxides are used.

The use of organic amines is not preferred.

Neutralizing agents which can be used are preferably inorganic bases, such as aqueous ammonia solution or sodium hydroxide or potassium hydroxide.

Preference is given to sodium hydroxide and potassium hydroxide.

The quantitative amount of the bases is 50 and 125 mol %, preferably between 70 and 100 mol % of the quantitative amount of the acid groups to be neutralized. The neutralization can also take place at the same time as the dispersion by the dispersion water already comprising the neutralizing agent.

Afterwards, in a further process step, in cases where it has still not happened or has only happened partially, the resulting prepolymer is dissolved with the help of aliphatic ketones such as acetone or 2-butanone.

The reaction of components A1) to A4) to give the prepolymer takes place partially or completely, but preferably completely. In this way, polyurethane prepolymers which contain free isocyanate groups are obtained without a diluent or in solution.

During the chain extension in stage B), $NH_2$- and/or NH-functional components are reacted with the remaining isocyanate groups of the prepolymer. Preferably, the chain extension/termination is carried out prior to the dispersion in water.

Suitable components B) for the chain extension are, in particular, organic di- or polyamines B1), such as, for example, ethylenediamine, 1,2- and 1,3-diaminopropane, 1,4-diaminobutane, 1,6-diaminohexane, isophoronediamine, isomer mixture of 2,2,4- and 2,4,4-trimethylhexamethylenediamine, 2-methylpentamethylenediamine, diethylenetriamine, diaminodicyclohexylmethane and/or dimethylethylenediamine.

Moreover, it is also possible to use compounds B1) which, besides a primary amino group, also have secondary amino groups or, besides an amino group (primary or secondary), also have OH groups. Examples thereof are primary/secondary amines, such as diethanolamine, 3-amino-1-methylaminopropane, 3-amino-1-ethylaminopropane, 3-amino-1-cyclohexylaminopropane, 3-amino-1-methylaminobutane, alkanolamines, such as N-aminoethylethanolamine, ethanolamine, 3-aminopropanol, neopentanolamine be used for the chain extension and/or termination.

For the chain termination, use is usually made of amines B1) having a group which is reactive towards isocyanates, such as methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine, and suitable substituted derivatives thereof, amidoamines of diprimary amines and monocarboxylic acids, monoketime of diprimary amines, primary/tertiary amines, such as N,N-dimethylaminopropylamine.

If anionic hydrophilizing agents corresponding to the definition of B2) with $NH_2$ or NH groups are used for the chain extension, the chain extension of the prepolymers preferably takes place before the dispersion.

The degree of chain extension, i.e. the equivalent ratio of NCO-reactive groups of the compounds used for the chain extension and chain termination to free NCO groups of the prepolymer is generally between 40 and 150%, preferably between 50 and 110%, particularly preferably between 60 and 100%.

The aminic components B1) and B2) can optionally be used in water- or solvent-diluted form in the process according to the invention individually or in mixtures, with any order of the addition being possible in principle.

If water or organic solvents are co-used as diluents, then the diluent content in the component used in B) for chain extension is preferably 40 to 95% by weight.

The dispersion preferably takes place after the chain extension. For this, the dissolved and chain-extended polyurethane polymer is optionally either introduced into the dispersion water with strong shear, such as, for example, with vigorous stirring, or, conversely, the dispersion water is stirred into the chain-extended polyurethane polymer solutions. Preferably, the water is added to the dissolved chain-extended polyurethane polymer.

The solvent still present in the dispersions after the dispersion step is then usually removed by distillation. Removal during dispersion is likewise possible.

The residual content of organic solvents in the polyurethane dispersions prepared in this way is typically less than 10% by weight, preferably less than 3% by weight, based on the total dispersion.

The pH of the aqueous polyurethane dispersions used according to the invention is typically less than 8.0, preferably less than 7.5 and is particularly preferably between 5.5 and 7.5.

Within the context of the present invention, the sun protection compositions can advantageously be present in the following forms: cream, lotion, milk, gel, oil, balm, aqueous solution.

The sun protection composition according to the invention comprises preferably 0.1 to 20% by weight of the polyurethane described above and in particular 0.5 to 10% by weight, in each case based on the total weight of the composition.

The sun protection composition according to the invention which comprises the polyurethane described above or its aqueous dispersion should satisfy the aforementioned properties of a sun protection product. Following application, the sun protection composition according to the invention naturally remains at least partially on the skin, and thus differs, for example, from cosmetic products which are removed following use on the skin, such as, for example, cosmetic face masks and cleansing products, such as soaps etc. The sun protection composition according to the invention, furthermore, generally also does not include haircare compositions, make-up compositions, such as make-up etc., make-up lipsticks and nail varnishes or the like.

Within the context of the present invention, the sun protection compositions are differentiated in particular by their consistency: cream (viscous), lotion and milk (flowable), gels (semisolid), oils, and also liquid formulations such as, for example, spray, balm and aqueous solutions.

The sun protection compositions may be present, for example, in the form of oil-in-water, water-in-oil, water-in-silicone, silicone-in-water, oil-in-water-in-oil, water-in-oil-in-water emulsion.

The sun protection composition can also be foamed using a propellant gas.

The emulsions described above can, for example, be stabilized by an O/W, W/O or W/Si emulsifier, thickener (such as, for example, hydrodispersion) or solids (such as, for example, Pickering emulsion).

The sun protection compositions can comprise one or more emulsifiers or surface-active agents.

Thus, in particular oil-in-water emulsions (O/W) according to the invention comprise at least one emulsifier with an HLB value of >7 and, if appropriate, a coemulsifier. O/W emulsifiers can advantageously be selected from the group of nonionic, anionic, cationic or amphoteric emulsifiers.

The nonionic emulsifiers include, for example:
a) partial fatty acid esters and fatty acid esters of polyhydric alcohols and ethoxylated derivatives thereof
b) ethoxylated fatty alcohols and fatty acids
c) ethoxylated fatty amines, fatty acid amides, fatty acid alkanolamides
d) alkylphenol polyglycol ethers (e.g. Triton® X)
e) ethoxylated fatty alcohol ethers.

Particularly advantageous nonionic O/W emulsifiers are ethoxylated fatty alcohols or fatty acids, preferably PEG-100 stearate, PEG-40 stearate, PEG-50 stearate, ceteareth-20, ceteth-20, steareth-20, ceteareth-12, ceteth-12, steareth-12, esters of mono-, oligo- or polysaccharides with fatty acids, preferably cetearyl glucoside, methylglucose distearate, glyceryl monostearates (self-emulsifying), sorbitan esters, such as, for example, sorbitan stearates (Tween® 20 and Tween® 60 from Uniqema), sorbitan palmitates (Span® 40, Uniqema), glyceryl stearyl citrates, sucrose esters, such as, for example, sucrose stearates, PEG-20 methyl glucose sequistearate), dicarboxylic acid esters of fatty alcohol (dimyristyl tartrate).

Advantageous anionic emulsifiers are soaps (e.g. sodium or triethanolamine salts of stearic acid or palmitic acid), esters of citric acid, such as glyceryl stearate citrate, fatty alcohol sulphates, and also mono-, di- and trialkyl phosphoric acid esters and ethoxylates thereof.

The cationic emulsifiers include quaternary ammonium compounds with a long-chain aliphatic radical, e.g. distearyl dimonium chloride.

The amphoteric emulsifiers include, for example:
a) alkylamininoalkane carboxylic acids
b) betaines, sulphobetaines
c) imidazoline derivatives.

Furthermore, there are naturally occurring emulsifiers, which include beeswax, wool wax, lecithin and sterols.

Suitable coemulsifiers for the O/W emulsions according to the invention which can be used are fatty alcohols having 8 to 30 carbon atoms, monoglycerol esters of saturated or unsaturated, branched or unbranched alkanecarboxylic acids with a chain length of from 8 to 24 carbon atoms, in particular 12 to 18 carbon atoms, propylene glycol esters of saturated or unsaturated, branched or unbranched alkanecarboxylic acids with a chain length of from 8 to 24 carbon atoms, in particular 12 to 18 carbon atoms, and also sorbitan esters of saturated or unsaturated, branched or unbranched alkanecarboxylic acids with a chain length of from 8 to 24 carbon atoms, in particular 12 to 18 carbon atoms.

Particularly advantageous coemulsifiers are glyceryl monostearate, glyceryl monooleate, diglyceryl monostearate, sorbitan monoisostearate, sucrose distearate, cetyl alcohol, stearyl alcohol, behenyl alcohol, isobehenyl alcohol and polyethylene glycol(2) stearyl ether (steareth-2).

Within the context of the present invention, it may be advantageous to use further emulsifiers. Thus, for example, the water resistance of the preparations according to the invention can be further increased in this way. Suitable emulsifiers are, for example, alkylmethicone copolyols and alkyldimethicone copolyols, in particular cetyldimethicone copolyol, laurylmethicone copolyol, W/O emulsifiers, such as sorbitan stearate, glyceryl stearate, glycerol stearate, sorbitan oleate, lecithin, glyceryl isostearate, polyglyceryl-3 oleate, polyglyceryl-3 diisostearate, PEG-7-hydrogenated castor oil, polyglyceryl-4 isostearate, acrylate/$C_{10-30}$-alkyl acrylate crosspolymer, sorbitan isostearate, poloxamer 101, polyglyceryl-2 dipolyhydroxystearate, polyglyceryl-3 di isostearate, polyglyceryl-4 dipolyhydroxystearate, PEG-30 dipolyhydroxystearate, diisostearoyl polyglyceryl-3 diisostearate, glycol distearate and polyglyceryl-3 dipolyhydroxystearate.

The compositions according to the invention, such as, in particular, the O/W compositions, can advantageously comprise thickeners of the water phase. Advantageous thickeners are:

Crosslinked or uncrosslinked acrylic acid or methacrylic acid homopolymers or copolymers. These include crosslinked homopolymers of methacrylic acid or acrylic acid, copolymers of acrylic acid and/or methacrylic acid and monomers which are derived from other acrylic or vinyl monomers, such as C10-30 alkyl acrylates, C10-30-alkyl methacrylates and vinyl acetate and vinylpyrrolidones.

Thickening polymers of natural origin, for example based on cellulose, guar gum, xanthan, scleroglucan, gellan gum, rhamsan and karaya gum, alginates, maltodextrin, starch and its derivatives, carob seed flour, hyaluronic acid, carrageenan.

Nonionic, anionic, cationic or amphoteric associative polymers, e.g. based on polyethylene glycols and their derivatives, or polyurethanes.

Crosslinked or uncrosslinked homopolymers or copolymers based on acrylamide or methacrylamide, such as homopolymers of 2-acrylamido-2-methylpropanesulphonic acid, copolymers of acrylamide or methacrylamide and methacryloyloxyethyltrimethylammonium chloride or copolymers of acrylamide and 2-acrylamido-2-methylpropanesulphonic acid.

Particularly advantageous thickeners are thickening polymers of natural origin, crosslinked acrylic acid or methacrylic acid homopolymers or copolymers and crosslinked copolymers of 2-acrylamido-2-methylpropanesulphonic acid.

Very particularly advantageous thickeners are xanthan gum, such as the products supplied under the names Keltrol® and Kelza® by CP Kelco or the products from RHODIA with the name Rhodopol, and guar gum, such as the products available under the name Jaguar® HP105 from RHODIA.

Very particularly advantageous thickeners are crosslinked homopolymers of methacrylic acid or acrylic acid which are commercially available from Lubrizol under the names Carbopol® 940, Carbopol® 941, Carbopol® 980, Carbopol® 981, Carbopol® ETD 2001, Carbopol® EDT 2050, Carbopol® 2984, Carbopol® 5984 and Carbopol® Ultrez 10, from 3V under the names Synthalen® K, Synthalen® L and Synthalen® MS.

Very particularly advantageous thickeners are crosslinked polymers of acrylic acid or methacrylic acid and a $C_{10-30}$-alkyl acrylate or $C_{10-30}$-alkyl methacrylate and copolymers of acrylic acid or methacrylic acid and vinylpyrrolidone. Such copolymers are commercially available, for example, from Lubrizol under the names Carbopol® 1342, Carbopol® 1382, Pemulen® TR1 or Pemulen® TR2 and from ISP under the names Ultrathix P-100 (INCI: Acrylic Acid/VP Crosspolymer).

Very particular advantageous thickeners are crosslinked copolymers of 2-acrylamido-2-methylpropanesulphonic acid. Such copolymers are available, for example, from Clariant under the names Aristoflex® AVC (INCI: Ammonium Acryloyldimethyltaurate/VP Copolymer).

These thickeners are generally present in a concentration of from about 0% to 2% by weight, preferably 0% to 1% by weight, based on the total weight of the composition according to the invention.

Further compositions according to the invention may be water-in-oil or water-in-silicone emulsions. Preference is given to water-in-oil (W/O) or water-in-silicone emulsions (W/Si) which comprise one or more silicone emulsifiers (W/S) with an HLB value of ≤8 or one or more W/O emulsifiers with an HLB value of <7 and optionally one or more O/W emulsifiers with an HLB value of >10.

The silicone emulsifiers can advantageously be selected from the group comprising alkyldimethicone copolyols, such as, for example, cetyl PEG/PPG 10/1 dimethicone copolyol (ABIL® EM 90 from Goldschmidt AG) or lauryl PEG/PPG-18/18 dimethicones (Dow Corning® 5200 from Dow Corning Ltd.) and dimethicone copolyols, such as, for example, PEG-10 dimethicones (KF-6017 from Shin Etsu), PEG/PPG-18/18 dimethicones (Dow Corning 5225C from Dow Corning Ltd.) or PEG/PPG-19/19 dimethicones (Dow Corning BY-11 030 from Dow Corning Ltd.) or trimethylsilylamodimethicones.

The W/O emulsifiers with an HLB value of <7 can advantageously be selected from the following group: fatty alcohols having 8 to 30 carbon atoms, monoglycerol esters of saturated and/or unsaturated, branched and/or unbranched alkanecarboxylic acids of chain length of from 8 to 24, in particular 12-18 carbon atoms, diglycerol esters of saturated and/or unsaturated, branched and/or unbranched alkanecarboxylic acids of chain length from 8 to 24, in particular 12-18, carbon atoms, monoglycerol ethers of saturated and/or unsaturated, branched and/or unbranched alcohols of chain length of from 8 to 24, in particular 12-18, carbon atoms, diglycerol ethers of saturated and/or unsaturated, branched and/or unbranched alcohols of chain length from 8 to 24, in particular 12-18, carbon atoms, propylene glycol esters of saturated and/or unsaturated, branched and/or unbranched alkanecarboxylic acids of chain length from 8 to 24, in particular 12-18, carbon atoms, and also sorbitan esters of saturated and/or unsaturated, branched and/or unbranched alkanecarboxylic acids of chain length from 8 to 24, in particular 12-18, carbon atoms.

Particularly advantageous W/O emulsifiers are: glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (steareth-2), glyceryl monolaurate, glyceryl monocaprate and glyceryl monocaprylate.

Further possible W/O emulsifiers are selected from the group of the compounds polyglyceryl-2 di polyhydroxystearate, PEG-30 di polyhydroxystearate, cetyldimethicone copolyol and polyglyceryl-3 diisostearate.

The O/W emulsifiers with an HLB value of >10 can advantageously be selected from the group comprising lecithin, trilaureth-4 phosphate, polysorbate-20, polysorbate-60, PEG-22 dodecyl glycol copolymer, sucrose stearate and sucrose laurate.

An oil thickener can advantageously be used for stabilizing the W/O emulsion according to the invention against sedimentation or flocculation of the water droplets.

Particularly advantageous oil thickeners are organomodified clays, such as organomodified bentonites (Bentone® 34 from Rheox), organomodified hectorites (Bentone® 27 and Bentone® 38 from Rheox) or organomodified montmorillonite, hydrophobic pyrogenic silica, where the silanol groups are substituted by trimethylsiloxy groups (AEROSIL® R812 from Degussa) or with dimethylsiloxy groups or polydimethylsiloxane (AEROSIL® R972, AEROSIL® R974 from Degussa, CAB-β-SIL® TS-610, "CAB-O-SIL® TS-720 from Cabot), magnesium or aluminium stearate, or styrene copolymers, such as, for example, styrene-butadiene-styrene, styrene-isopropene-styrene, styrene-ethylene/butene-styrene or styrene-ethylene/propene-styrene.

The thickener for the fatty phase can be present in an amount of from 0.1 to 5% by weight, based on the total weight of the emulsion, and better 0.4 to 3% by weight.

The aqueous phase can also comprise stabilizers. The stabilizer can be, for example, sodium chloride, magnesium chloride or magnesium sulphate and mixtures thereof.

Oils can be used in W/O, W/Si and O/W emulsions.

If present, the fatty phase of the composition according to the invention can comprise one non-volatile oil and/or volatile oils and waxes. The O/W composition comprises advantageously 0.01 to 45% by weight of oils, based on the total weight of the composition, and particularly advantageously 0.01 to 20% by weight of oils. The W/O or W/Si composition advantageously comprises at least 20% by weight of oils, based on the total weight of the composition.

The non-volatile oil is advantageously selected from the group of mineral, animal, vegetable or synthetic origin, polar or nonpolar oils and mixtures thereof.

The lipid phase of the cosmetic or dermatological emulsions according to the invention can advantageously be selected from the following group of substances:
mineral oils, mineral waxes, polar oils, such as triglycerides of capric acid or of caprylic acid, also natural oils, such as, for example, castor oil, fats, waxes and other natural and synthetic fatty bodies, preferably esters of fatty acids with alcohols of low carbon number, e.g. with isopropanol, propylene glycol or glycerol, or esters of fatty alcohols with alkanoic acids of low carbon number or with fatty acids; alkyl benzoates; silicone oils, such as dimethylpolysiloxanes, diethylpolysiloxanes, diphenylpolysiloxanes, and mixed forms thereof.

The polar oils are advantageously selected from the group:
a) esters of saturated and/or unsaturated, branched and/or unbranched alkanecarboxylic acids of chain length from 3 to 30 carbon atoms and saturated and/or unsaturated, branched and/or unbranched alcohols of chain length from 3 to 30 carbon atoms,
b) esters of aromatic carboxylic acids and saturated and/or unsaturated, branched and/or unbranched alcohols of chain length from 3 to 30 carbon atoms.

Such ester oils can then advantageously be selected from the group:
isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, isotridecyl isononanoate, 2-ethylhexyl palmitate, 2-ethylhexyl laurate, 2-ethylhexyl isostearate, 2-hexyldecyl stearate, 2-octyldodecyl palmitate, 2-ethylhexyl cocoate, oleyl oleate, oleyl erucate, erucyl oleate, erucyl erucate, dicaprylyl carbonate (Cetiol® CC) and cocoglycerides (Myritol® 331), and also synthetic, semisynthetic and natural mixtures of such esters, e.g. jojoba oil.
c) alkyl benzoates C12-15-alkyl benzoate (Finsolv® TN from Finetex) or 2-phenylethyl benzoate (X-Tend® 226 from ISP)
d) lecithins and the fatty acid triglycerides, namely the triglycerol esters of saturated and/or unsaturated, branched and/or unbranched alkanecarboxylic acids of chain length from 8 to 24, in particular 12 to 18 carbon atoms. For example, the fatty acid triglycerides can be selected from the group of cocoglyceride, olive oil, sunflower oil, soybean oil, peanut oil, rapeseed oil, almond oil, palm oil, coconut oil, castor oil, wheat germ oil, grapeseed oil, safflower oil, evening primrose oil, macadamia nut oil, apricot kernel oil, avocado oil and the like.
e) the dialkyl ethers and dialkyl carbonates, e.g. dicaprylyl ether (Cetiol® OE from Cognis) and/or dicaprylyl carbonate (for example Cetiol® CC from Cognis) are advantageous.
f) saturated or unsaturated, branched or unbranched alcohols, such as, for example, octyldodecanol.

The non-volatile oil can likewise advantageously also be a nonpolar oil which is selected from the group of branched and unbranched hydrocarbons, in particular mineral oil, vaseline oil, paraffin oil, squalane and squalene, polyolefins, for example polydecenes, hydrogenated polyisobutenes, C13-16 isoparaffin and isohexadecane.

The nonpolar non-volatile oil can be selected among the non-volatile silicone oils.

Of the non-volatile silicone oils, the polydimethylsiloxanes (PDMS), which are optionally phenylated, such as phenyltrimethicone, or are optionally substituted with aliphatic and/or aromatic groups or with functional groups, for example hydroxyl groups, thiol groups and/or amino groups; polysiloxanes modified with fatty acids, fatty alcohols or polyoxyalkylenes and mixtures thereof can be given.

Particularly advantageous oils are 2-ethylhexyl isostearate, octyldodecanol, isotridecyl isononanoate, isoeicosane, 2-ethylhexyl cocoate, C12-15 alkyl benzoate, caprylic/capric triglyceride, dicaprylyl ether, mineral oil, dicaprylyl carbonate, cocoglycerides, butylene glycol dicaprylate/dicaprate, hydrogenated polyisobutenes, cetaryl isononanoates, isodecyl neopentanoates, squalane, C13-16 isoparaffin.

The composition according to the invention can also comprise a wax.

Within the context of the present specification, a wax is defined as a lipophilic fatty substance which is solid at room temperature (25° C.) and exhibits a reversible solid/liquid change in state at a melting temperature between 30° C. and 200° C. Above the melting point, the wax becomes low viscosity and miscible with oils.

The wax is advantageously selected from the groups of natural waxes, such as, for example, cotton wax, carnauba wax, candelilla wax, esparto wax, Japan wax, Montan wax, sugarcane wax, beeswax, wool wax, shellac, microwaxes, ceresine, ozokerite, ouricury wax, cork fibre wax, lignite waxes, berry wax, shea butter or synthetic waxes, such as paraffin waxes, polyethylene waxes, waxes produced by Fischer-Tropsch synthesis, hydrogenated oils, fatty acid esters and glycerides which are solid at 25° C., silicone waxes and derivatives (alkyl derivatives, alkoxy derivatives, and/or esters of polymethylsiloxane) and mixtures thereof. The waxes can be present in the form of stable dispersions of colloidal wax particles which can be prepared by known processes, for example as in "Microemulsions Theory and Practice", L. M. Prince Ed., Academic Press (1977), pages 21-32.

Waxes may be present in amounts of from 0 to 10% by weight, based on the total weight of the composition, and preferably 0 to 5% by weight.

The composition according to the invention can also comprise a volatile oil which is selected from the group of volatile hydrocarbon oils, siliconized oils or fluorinated oils. The volatile oil can be present in an amount of from 0 to 25% by weight, based on the total weight of the emulsion, preferably 0 to 20% by weight and even more preferably 0 to 15% by weight.

Within the context of the present specification, a volatile oil is an oil which, upon contact with the skin at room temperature and atmospheric pressure, evaporates in less than one hour. The volatile oil is liquid at room temperature and, at room temperature and atmospheric pressure, has a vapour pressure of from 0.13 to 40 000 Pa ($10^{-3}$ to 300 mmHg), preferably 1.3 to 13 000 Pa (0.01 to 100 mmHg) and particularly preferably 1.3 to 1300 Pa (0.01 to 10 mmHg) and a boiling point of from 150 to 260° C. and preferably 170 to 250° C.

A hydrocarbon oil is understood as meaning an oil which is formed essentially from carbon atoms and hydrogen atoms and optionally oxygen atoms or nitrogen atoms and contains no silicon atoms or fluorine atoms, where it may also consist of carbon atoms and hydrogen atoms; however, it can also contain ester groups, ether groups, amino groups or amide groups.

A siliconized oil is understood as meaning an oil which contains at least one silicon atom and in particular Si—O groups.

A fluorinated oil is to be understood as meaning an oil which contains at least one fluorine atom.

The volatile hydrocarbon oil according to the invention can be selected from the hydrocarbon oils with a flash point of from 40 to 102° C., preferably 40 to 55° C. and even more preferably 40 to 50° C.

For example, the volatile hydrocarbon oils are those with 8 to 16 carbon atoms and mixtures thereof, in particular branched $C_{8-16}$-alkanes, such as the isoalkanes (which are also referred to as isoparaffins) with 8 to 16 carbon atoms, isododecane, isodecane, isohexadecane and, for example, the oils which are supplied under the tradenames Isopars® or Permethyls®; and the branched $C_{8-16}$-esters, such as isohexyl neopentanoate and mixtures thereof.

The volatile hydrocarbon oils such as isododecane, isodecane and isohexadecane are particularly advantageous.

The volatile siliconized oil according to the invention can be selected from the siliconized oils with a flash point of from 40 to 102° C., preferably a flash point above 55° C. and at most 95° C. and particularly preferably in the range from 65 to 95° C.

For example, the volatile siliconized oils are straight-chain or cyclic silicone oils having 2 to 7 silicon atoms, where these silicones optionally contain alkyl or alkoxy groups having 1 to 10 carbon atoms.

The volatile siliconized oils such as octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and mixtures thereof are particularly advantageous.

The volatile fluorinated oil generally has no flash point.

For example, the volatile fluorinated oils are nonafluoroethoxybutane, nonafluoromethoxybutane, decafluoropentane, tetradecafluorohexane, dodecafluoropentane and mixtures thereof.

The cosmetic acceptable medium of the composition according to the invention comprises water and optionally a cosmetically suitable water-miscible organic solvent.

The water used in the composition according to the invention may be a blossom water, pure demineralized water, mineral water, thermal water and/or seawater.

In the case of an O/W composition, the water fraction can be in the range from 40 to 95% by weight, preferably in the range from 50 to 90% by weight, very particularly in the range from 60 to 80% by weight, based on the total weight of the composition. In the case of a W/O composition, the water fraction is in the range from 0 to 60% by weight, preferably in the range from 10 to 50% by weight, very preferably in the range from 30 to 50% by weight, based on the total weight of the composition.

The preferred solvents are, for example, the aliphatic alcohols with C1-4 carbon atoms, such as ethanol and isopropanol; polyol and derivatives thereof, such as propylene glycol, dipropylene glycol, butylene-1,3 glycol, polypropylene glycol, glycol ethers such as alkyl (C1-4) ethers of mono-, di- or tripropylene glycol or mono-, di- or triethylene glycol, and mixtures thereof.

The quantitative fraction of the solvent or solvents in the composition according to the invention can be, for example, in the range from 0 to 25% by weight and preferably 0 to 10% by weight, based on the total weight of the composition.

The sun protection composition according to the invention comprises a total of 16 to 35% by weight, preferably 20 to 35% by weight, particularly preferably 20 to 30% by weight, of sun protection filter substances, based on the total weight of the sun protection composition. The stated amounts are the sum of the amounts of all sun protection filter substances present in the sun protection composition according to the invention. Sun protection filter substances can also be referred to as sun protection filters or substances conferring sun protection.

The sun protection filters are in particular UV filters which filter light in the UV wavelength region, in particular of less than 400 nm. The UV wavelength region is usually divided as follows:

| UV light | Wavelength range in nm |
| --- | --- |
| Near UV | 400-200 nm |
| UV-A | 380-315 nm |
| UV-B | 315-280 nm |
| UV-C | 280-100 nm |
| Far UV, vacuum radiation | 200-10 nm |
| Extreme UV | 31-1 nm |

The sun protection filters (or UV filters) can be selected from the organic filters, the physical filters and mixtures thereof.

The sun protection composition according to the invention can comprise in particular UV-A filters, UV-B filters, broadband filters and/or physical filters as sun protection filter substances. The sun protection composition according to the invention preferably comprises mixtures of at least two of these aforementioned types of sun protection filter substances. The sun protection composition according to the invention can also comprise a plurality of sun protection filter substances which are assigned to one of these types of sun protection filter substances, i.e. e.g. a plurality of UV-A filters and/or a plurality of UV-B filters. Any desired combinations are possible here.

The UV filters used can be oil-soluble or water-soluble. The following list of specified UV filters is of course not limiting.

Examples of the UV-B filters are:
(1) salicylic acid derivatives, particularly homomethyl salicylate, octyl salicylate and 4-isopropylbenzyl salicylate;
(2) cinnamic acid derivatives, in particular 2-ethylhexyl p-methoxycinnamate, which is available from Givaudan under the name Parsol MCX® and isopentyl 4-methoxycinnamate;
(3) liquid β,β'-diphenylacrylate derivatives, in particular 2-ethylhexyl α,β-diphenylacrylate or octocrylene, which is available from BASF under the name UVINUL N539®;
(4) p-aminobenzoic acid derivatives, in particular 2-ethylhexyl 4-(dimethylamino)benzoate, amyl 4-(dimethylamino)benzoate;
(5) 3-benzylidenecamphor derivatives, in particular 3-(4-methylbenzylidene)camphor which is commercially available from Merck under the name EUSOLEX 6300®, 3-benzylidenecamphor, benzylidenecamphor sulphonic acid and polyacrylamidomethyl-benzylidenecamphor;
(6) 2-phenylbenzimidazole-5-sulphonic acid, which is available under the name EUSOLEX 232® from Merck;
(7) 1,3,5-triazine derivatives, in particular: -2,4,6-tris[p-(2'-ethylhexyl-1'-oxycarbonyl)anilino]-1,3,5-triazine, which is supplied by BASF under the name UVINUL T150®, and -dioctylbutamidotriazone, which is supplied by Sigma 3V under the name UVASORB HEB®;
(8) esters of benzalmalonic acid, in particular di(2-ethylhexyl) 4-methoxybenzalmalonate and 3-(4-(2,2-bisethoxycarbonylvinyl)-phenoxy)propenyl)methoxysiloxane/dimethylsiloxane copolymer, which is available from Roche Vitamines under the name Parsol® SLX; and
(9) the mixtures of these filters.

The sun protection composition according to the invention comprises, as at least one sun protection filter substance, preferably as at least one UV-B filter, octocrylene in an amount of from 4 to 12% by weight, preferably from 5 to 12% by weight, particularly preferably from 6 to 12% by weight, very particularly preferably from 7 to 11% by weight, based on the total weight of the sun protection composition, and, in one preferred embodiment, in an amount of from 8 to 11% by weight, based on the total weight of the sun protection composition.

Examples of UV-A filters are:
(1) dibenzoylmethane derivatives, particularly 4-(t-butyl)-4'-methoxydibenzoylmethane, which is supplied by Givaudan under the name PARSOL 1789® and 1-phenyl-3-(4'-isopropylphenyl)propane-1,3-dione;
(2) benzene-1,4-[di(3-methylidenecamphor-10-sulphonic acid)], optionally completely or partially neutralized, commercially available under the name MEXORYL SX® from Chimex.
(3) hexyl 2-(4'-diethylamino-2'-hydroxybenzoyl)benzoate (also aminobenzophenone);
(4) silane derivatives or polyorganosiloxanes with benzophenone groups;
(5) anthranilates, particularly menthyl anthranilate, which is supplied by Symrise under the name NEO HELIOPAN MA®;
(6) compounds which contain at least two benzoazolyl groups or at least one benzodiazolyl group per molecule, in particular 1,4-bis-benzimidazolylphenylene-3,3',5,5'-tetrasulphonic acid and its salts, which are commercially available from Symrise;
(7) silicon derivatives of benzimidazolylbenzazoles, which are N-substituted, or of benzofuranylbenzazoles, in particular:
2-[1-[3-[1,3,3,3-tetramethyl-1-[(trimethylsilyl)oxy]disiloxanyl]propyl]-1H-benzimidazol-2-yl]benzoxazole;
2-[1-[3-[1,3,3,3-tetramethyl-1-[(trimethylsilyl)oxy]disiloxanyl]propyl]-1H-benzimidazol-2-yl]benzothiazole;
2-[1-(3-trimethylsilanylpropyl)-1H-benzimidazol-2-yl]benzoxazole;
6-methoxy-1,1'-bis(3-trimethylsilanylpropyl)1H,1'H-[2,2']dibenzimidazolylbenzoxazole;
2-[1-(3-trimethylsilanylpropyl)-1H-benzimidazol-2-yl]benzothiazole;
which are described in the patent application EP-A-1 028 120;
(8) triazine derivatives, in particular 2,4-bis[5-1(dimethylpropyl)benzoxazol-2-yl-(4-phenyl)imino]-6-(2-ethylhexyl)imino-1,3,5-triazine, which is supplied by 3V under the name Uvasorb® K2A; and
(9) mixtures thereof.

In one preferred embodiment, the sun protection composition according to the invention comprises, as sun protection filter substance, preferably as at least one UV-A filter, at least one dibenzoylmethane derivative, preferably 4-(t-butyl)-4'-methoxydibenzoylmethane. This dibenzoylmethane derivative, preferably 4-(t-butyl)-4'-methoxydibenzoylmethane, can preferably be present in the sun protection composition according to the invention preferably in an amount of from 1 to 5% by weight, particularly preferably from 2 to 5% by weight, based on the total weight of the sun protection composition.

Examples of broadband filters are:
(1) benzophenone derivatives, for example
2,4-dihydroxybenzophenone (benzophenone-1);
2,2',4,4'-tetrahydroxybenzophenone (benzophenone-2);
2-hydroxy-4-methoxybenzophenone (benzophenone-3), available from BASF under the name UNIVNUL M40®;
2-hydroxy-4-methoxybenzophenone-5-sulphonic acid (benzophenone-4), and its sulphonate form (benzonphenone-5), commercially available from BASF under the name UVINUL MS40®;
2,2'-dihydroxy-4,4'-dimethoxybenzophenone (benzophenone-6-);
5-chloro-2-hydroxybenzophenone (benzophenone-7-);
2,2'-dihydroxy-4-methoxybenzophenone (benzophenone-8);
the disodium salt of 2,2'-dihydroxy-4,4'-dimethoxybenzophenone-5,5'-disulphonic acid (benzophenone-9-);

2-hydroxy-4-methoxy-4'-methylbenzophenone (benzophenone-10); benzophenone-11;
2-hydroxy-4-(octyloxy)benzophenone (benzophenone-12).
(2) triazine derivatives, in particular 2,4-bis{[4-2-ethylhexyloxy)-2-hydroxy]-phenyl}-6-(4-methoxyphenyl)-1,3,5-triazine, which is supplied by Ciba Geigy under the name TINOSORB S®, and 2,2'-methylenebis[6-(2H-benzotriazol-2-yl)4-(1,1,3,3-tetramethylbutyl)phenol], which is available from Ciba Geigy under the name TINOSORB M®; and
(3) 2-(1H-benzotriazol-2-yl)-4-methyl-6-[2-methyl-3-[1,3,3,3-tetramethyl-1-[(trimethylsilyl)oxy]disiloxanyl]propyl]phenol with the INCI name Drometrizole Trisiloxane.

It is also possible to use a mixture of two or more filters and a mixture of UV-B filters, UV-A filters and broadband filters, and also mixtures with physical filters.

Among the physical filters, the sulphates of barium, oxides of titanium (titanium dioxide, amorphous or crystalline in the form of rutile and/or anatase), of zinc, of iron, of zirconium, of cerium, silicon, manganese or mixtures thereof may be given, for example. The metal oxides can be present in particle form with a size in the micrometer range or nanometer range (nanopigments). The average particle sizes for the nanopigments are, for example, 5 to 100 nm.

In preferred embodiments, the sun protection compositions according to the invention have a sun protection factor (SPF) of more than 15, preferably of more than 20, measured according to the International Sun Protection Factor (SPF) test method in accordance with COLIPA. This measurement method is known to the person skilled in the art.

The sun protection compositions according to the invention may additionally comprise one or more further additives which are customary in cosmetics, such as antioxidants, and/or other auxiliaries and additives, such as, for example, emulsifiers, interface-active substances, antifoams, thickeners, surfactants, active ingredients, humectants, filler, film formers, solvents, coalescing agents, aroma substances, odour absorbers, perfumes, gel formers and/or other polymer dispersions, such as, for example, dispersions based on polyacrylates, fillers, softeners, pigments, dyes, flow agents, thixotropic agents, suppleness agents, softeners, preservatives etc. The amounts of the various additives are known to the person skilled in the art for the range to be used and are, for example, in the range from 0 to 25% by weight, based on the total weight of the composition.

The sun protection composition according to the invention can also comprise sensory additive. Sensory additives are to be understood as meaning in particular colourless or white, mineral or synthetic, lamellar, spherical or elongated inert particles or a nonparticulate sensory additive which, for example, further improve the sensory properties of the formulations and, for example, leave behind a velvety or silky skin feel.

The sensory additives can be present in the composition according to the invention for example in an amount of up to 10% by weight, preferably 0.1 to 10% by weight and more preferably 0.1 to 7% by weight, based on the total weight of the composition.

Advantageous particulate sensory additives within the context of the present invention are talc, mica, silicon dioxide, kaolin, starch and derivatives thereof (for example tapioca starch, distarch phosphate, aluminium and sodium starch octenyl succinate and the like), pyrogenic silica, pigments which have neither primarily a UV-filter effect nor colouring effect (such as e.g. boron nitride etc.), boron nitride, calcium carbonate, dicalcium phosphate, magnesium carbonate, magnesium hydrogen-carbonate, hydroxyapatites, microcrystalline cellulose, powders of synthetic polymers, such as polyamides (for example the polymers available under the trade name "Nylon®"), polyethylene, poly-β-alanine, polytetrafluoroethylene ("Teflon®"), polyacrylate, polyurethane, lauroyl-lysine, silicone resin (for example the polymers available under the trade name "Tospearl®" from Kobo Products Inc.), hollow particles of polyvinylidene/acrylonitriles (Expancel® from Akzo Nobel) or hollow particles of silicon oxide (Silica Beads® from MAPRECOS).

Advantageous nonparticulate sensory additives can be selected from the group of dimethiconols (e.g. Dow Corning 1503 Fluid from Dow Corning Ltd.), silicone copolymers (e.g. divinyldimethicone/dimethicone copolymer, Dow Corning HMW 2220 from Dow Corning Ltd.) or silicone elasters (e.g. dimethicone crosspolymer, Dow Corning 9040 Silicone Elastomer Blend from Dow Corning Ltd.).

The sun protection composition according to the invention can furthermore comprise one or more humectants (moisturizers). Particularly advantageous humectants within the context of the present invention are, for example, glycerol, polyglycerol, sorbitol, dimethyl isosorbide, lactic acid and/or lactates, in particular sodium lactate, butylene glycol, propylene glycol, biosaccharide gum-1, glycine soya, hydroxyethylurea, ethylhexyloxyglycerol, pyrrolidonecarboxylic acid and urea. In addition, it is especially advantageous to use polymeric moisturizers from the group of water-soluble and/or water-swellable and/or water-gellable polysaccharides. For example, hyaluronic acid, chitosan and/or a fucose-rich polysaccharide, which is available under the name Fucogel™ 1000 from SOLABIA S.A., are especially advantageous.

Within the context of the present invention, antioxidants, such as for example, water-soluble antioxidants can be used particularly advantageously, such as, for example, vitamins, e.g. ascorbic acid and derivatives thereof. Vitamin E and derivatives thereof, and also vitamin A and derivatives thereof are very particularly advantageous.

Further advantageous active ingredients in the composition according to the invention include: α-hydroxycarboxylic acids, such as glycolic acid, lactic acid, malic acid, tartaric acid, citric acid and mandelic acid, β-hydroxycarboxylic acids, such as salicylic acid, and acylated derivatives thereof, 2-hydroxyalkanoic acid and its derivatives; natural active ingredients and/or derivatives thereof, such as, for example, alpha-lipoic acid, folic acid, phytoene, D-biotin, coenzyme Q10, alpha-glucosylrutin, carnitine, carnosine, natural and/or synthetic isoflavonoids, creatin, creatinine, taurine and/or [beta]-alanine and also 8-hexadecene-1,16-dicarboxylic acid (dioic acid, CAS number 20701-68-2; provisional INCI name Octadecenedioic acid) and/or Licochalcon A and the plant extracts.

The use of such special combinations of polyurethanes with special sun protection filter substances, and also the SPF boosting effect that is surprisingly to be observed here, have hitherto not been described in the prior art.

The present invention therefore further provides the use of a composition comprising at least one polyurethane obtainable by reacting one or more water-insoluble, non-water-dispersible, isocyanate-functional polyurethane prepolymers A) with one or more amino-functional compounds B), and a total of 16 to 35% by weight of sun protection filter substances, based on the total weight of the sun protection composition, wherein one of these sun protection filter substances is octocrylene which is present in an amount of from 4 to 12% by weight, based on the total weight of the sun protection composition, as sun protection composition and/or for the preparation of cosmetic sun protection compositions.

A cosmetic method for protecting the skin against negative effects of solar radiation, in which compositions comprising special combinations of polyurethanes with special sun protection filter substances is applied to the skin and, surprisingly, the SPF-boosting effect described previously arises, has also hitherto not been described in the prior art.

The present invention therefore further provides a cosmetic method for protecting the skin against negative effects of solar radiation, which involves applying a composition comprising at least one polyurethane obtainable by reacting one or more water-insoluble, non-water-dispersible, isocyanate-functional polyurethane prepolymers A) with one or more amino-functional compounds B), and a total of 16 to 35% by weight of sun protection filter substances, based on the total weight of the sun protection composition, wherein one of these sun protection filter substances is octocrylene which is present in an amount of from 4 to 12% by weight, based on the total weight of the sun protection composition, to the skin.

In particular, in this cosmetic method, the composition, following application to the skin, at least partially remains on it.

The present invention is illustrated by reference to examples, although these are not to be understood as being limiting. Unless stated otherwise, all of the quantitative data, fractions and percentages are based on the weight and the total amount or on the total weight of the compositions.

Unless indicated otherwise, all of the percentages are based on the weight.

Unless noted otherwise, all of the analytical measurements refer to measurements at temperatures of 23° C.

The solid or solid-body contents are determined by heating a weighed sample at 125° C. to constant weight. At constant weight, the solid-body content is calculated by reweighing the sample.

Unless expressly mentioned otherwise, NCO contents were determined volumetrically in accordance with DIN-EN ISO 11909.

The control on free NCO groups was carried out by means of IR spectroscopy (band at 2260 cm$^{-1}$).

The stated viscosities were determined by means of rotary viscometry in accordance with DIN 53019 at 23° C. using a rotary viscometer from Anton Paar Germany GmbH, Ostfildern, Germany.

The average particle sizes (the number-average is given) of the polyurethane dispersions were determined following dilution with deionized water by means of laser correlation spectroscopy (instrument: Malvern Zetasizer 1000, Malver Inst. Limited).

The in vivo measurement of the SPF was carried out in accordance with the International Sun Protection Factor (SPF) test method according to COLIPA/CTFA SA/JCIA and CTFA (May 2006).

Measurement Conditions:
UV source: xenon lamp (solar light type multiport 601.300 W)+filter WG 320
Irradiation spectrum: 290 to 400 nm
Application: 2 mg/cm$^2$±2.5%, application area=35 cm$^2$
Validation by P3 reference formulation (SPF between 13.8 and 18.7)
MED (minimal erythema dose): visual determination 20 hours±4 after exposure.

The in vitro measurement of the SPF was carried out in accordance with the COLIPA Guideline 2007a.

Measurement Conditions:
Application: 0.75 mg/cm$^2$ on a roughened PMMA surface (Plexiglas XT colorless 24770 UVD, supplier Schönberg Plexiglas HH)
UV source (for transmission and exposure): solar simulator
Substances Used:
Baycusan® C 1000 (Bayer MaterialScience AG, Leverkusen, Del.):
aqueous dispersion of a polyurethane with solids content of 40±2% by weight, viscosity of ≤500 mPas, pH of 7.5±1, prepared from a water-insoluble, non-water-dispersible, isocyanate-functional polyurethane prepolymer (obtained from a polyester of adipic acid, hexanediol, neopentyl glycol and hexamethyl diisocyanate) and ethylenediamine and diaminosulfonate as aminofunctional compounds.

Examples 1-3

The formulations 1 to 3 according to Tab. 1 were prepared by heating the aqueous phase to 80° C. with stirring, mixing the oil phase in a separate vessel with stirring and simultaneous heating to 80° C., then adding the oil phase, with continuous stirring, to the aqueous phase, and homogenizing the resulting emulsion. At 25° C., the amount of polyurethane dispersion Baycusan® C 1000 corresponding to the data in Tab. 1 was then added and mixed with the emulsion. The resulting emulsion was then homogenized again.

For the formulations 1 to 3, the SPF values were determined in such a way that both the SPF of the emulsion without the polyurethane dispersion and under identical conditions of the SPF of the emulsion with polyurethane dispersion was determined. The SPF of the emulsions for the formulations 1 and 2 was determined in vitro, and the SPF of the emulsion for the formulation 3 was determined in vivo. The results are summarized in Tab. 2. The ascertained values clearly show the SPF-boosting effect of the UV filter combination according to the invention. Moreover, despite the high UV filter combination, the formulations 2 to 3 exhibit a very good skin feel.

TABLE 1

Examples of formulations with UV filter combinations according to the invention

| Example | 1 | 2 | 3 |
|---|---|---|---|
| Baycusan ® C 1000 | 5.0 | 10.0 | 5.0 |
| Polyglyceryl-3 methylglucose distearate | 1 | 1 | |
| Sorbitan stearate | | | 1 |
| Glyceryl stearate | | | 1 |
| PEG-100 stearate | | | 1 |
| Cetearyl alcohol | 1 | 1 | |
| Ethylhexyl salicylate | 5 | 5 | |
| Homosalate | 10 | 10 | |
| Ammonium acryloyldimethyltaurate/VP copolymer (Aristoflex AVC, Clariant) | | | 0.30 |
| Decyl cocoate | | | 3.75 |
| Cetearyl ethylhexanoate | | | 3.75 |
| Xanthan gum | 0.2 | 0.2 | |
| Tocopheryl acetate | | | 0.40 |
| Neopentyl glycol diheptanoate | 2.5 | 2.5 | |
| C12-15 alkyl benzoate | 2.5 | 2.5 | |
| Dimethicone | 1 | 1 | 3.75 |
| Glycerol | 3 | 3 | |
| Ethylhexylglycerol | 1 | 1 | 1 |
| 4-(t-butyl)-4'-methoxydibenzoylmethane | 3 | 3 | 2.5 |
| Ethylhexyl methoxycinnamate | | | 7 |
| Octocrylene | 10 | 10 | 9 |
| Titanium dioxide | | | 5 |
| Disodium EDTA | 0.05 | 0.05 | 0.10 |
| Aqua | ad 100 | ad 100 | ad 100 |

TABLE 2

Results of the SPF measurement

| Example | SPF without polyurethane dispersion | SPF with polyurethane dispersion |
| --- | --- | --- |
| 1 | 19.8 | 24.7 |
| 2 | 19.8 | 27.8 |
| 3 | 17.7 | 26.0 |

The invention claimed is:

1. A sun protection composition comprising at least one polyurethane urea obtained by
   A) preparing water-insoluble, non-water-dispersible, isocyanate-functional polyurethane prepolymers A) from
      A1) organic polyisocyanates,
      A2) polymeric polyols with number-average molecular weights of from 400 to 8000 g/mol, determined by gel permeation chromatography relative to polystyrene standard in tetrahydrofuran at 23° C. and OH functionalities of 1.5 to 6,
      A3) optionally hydroxy-functional compounds with molecular weights of 62 to 399 g/mol, and
      A4) optionally nonionic hydrophilizing agents,
   and
   B) then reacting some or all of their free NCO groups with at least one amino-functional compound B), comprising at least one amino-functional compound B2) which comprises one or more ionic and/or ionogenic groups,
wherein the at least one polyurethane urea is dispersed in water during or after step B), wherein the isocyanate-functional polyurethane prepolymers A) have a content of ionic and ionogenic groups below 1 milliequivalent per 100 g of polyurethane prepolymers, and
wherein said sun protection composition comprises a total of 16 to 35% by weight of one or more sun protection filter substances, based on the total weight of said sun protection composition, and at least one of said sun protection filter substances is octocrylene which is present in an amount of from 4 to 12% by weight, based on total weight of said sun protection composition, wherein the at least one polyurethane urea has repeat units containing urea groups, which are formed in the reaction of the isocyanate-functional prepolymers A) with the at least one amino-functional compound B), and wherein the sun protection composition has a Sun Protection Factor (SPF) boosting effect.

2. The sun protection composition as claimed in claim 1, wherein said sun protection filter substances comprise one or more UV-A filters, UV-B filters, broadband filters and/or physical filters.

3. The sun protection composition as claimed in claim 1, wherein said sun protection composition comprises a total of 20 to 35% by weight of said sun protection filter substances, based on total weight of said sun protection composition.

4. The sun protection composition as claimed in claim 1, wherein said sun protection composition comprises octocrylene in an amount of from 6 to 12% by weight based on total weight of said sun protection composition.

5. The sun protection composition as claimed in claim 1, wherein said sun protection composition comprises a sun protection factor of at least 15 as measured in accordance with the SPF test method.

6. The sun protection composition as claimed in claim 1, wherein said amino-functional compound B) further comprises at least one amino-functional compound B1) which comprises no ionic and/or ionogenic groups.

7. The sun protection composition as claimed in claim 1, wherein said prepolymers A) are obtained by reacting at least one polyol selected from the group consisting of polyether polyols, polycarbonate polyols, polyether-polycarbonate polyols and/or polyester polyols, and polyisocyanates.

8. The sun protection composition as claimed in claim 1, wherein said at least one polyurethane urea comprises at least one sulphonic acid and/or sulphonate group.

9. The sun protection composition as claimed in claim 1, wherein said sun protection filter substances comprise at least one dibenzoylmethane derivative.

10. A method for preparing a cosmetic sun protection composition comprising mixing (i) at least one polyurethane urea obtained by
   A) preparing water-insoluble, non-water-dispersible, isocyanate-functional polyurethane prepolymers A) from
      A1) organic polyisocyanates,
      A2) polymeric polyols with number-average molecular weights of from 400 to 8000 g/mol, determined by gel permeation chromatography relative to polystyrene standard in tetrahydrofuran at 23° C. and OH functionalities of 1.5 to 6,
      A3) optionally hydroxy-functional compounds with molecular weights of 62 to 399 g/mol, and
      A4) optionally nonionic hydrophilizing agents,
   and
   B) then reacting some or all of their free NCO groups with at least one amino-functional compound B), comprising at least one amino-functional compound B2) which comprises one or more ionic and/or ionogenic groups, and (ii) a total of 16 to 35% by weight of one or more sun protection filter substances, based on total weight of said sun protection composition, wherein the at least one polyurethane urea is dispersed in water during or after step B), wherein the isocyanate-functional polyurethane prepolymers A) have a content of ionic and ionogenic groups below 1 milliequivalent per 100 g of polyurethane prepolymers, and
wherein one of said sun protection filter substances is octocrylene which is present in an amount of from 4 to 12% by weight, based on total weight of the sun protection composition, and
wherein the at least one polyurethane urea has repeat units containing urea groups, which are formed in the reaction of the isocyanate-functional prepolymers A) with the at least one amino-functional compound B), and wherein the sun protection composition has a SPF-boosting effect.

11. A cosmetic method for protecting skin against negative effects of solar radiation, comprising applying a composition comprising at least one polyurethane urea obtained by
   A) preparing water-insoluble, non-water-dispersible, isocyanate-functional polyurethane prepolymers A) from
      A1) organic polyisocyanates,
      A2) polymeric polyols with number-average molecular weights of from 400 to 8000 g/mol, determined by gel permeation chromatography relative to polystyrene standard in tetrahydrofuran at 23° C. and OH functionalities of 1.5 to 6,
      A3) optionally hydroxy-functional compounds with molecular weights of 62 to 399 g/mol, and
      A4) optionally nonionic hydrophilizing agents,
   and
   B) then reacting some or all of their free NCO groups with at least one amino-functional compound B), comprising at least one amino-functional compound B2) which comprises one or more ionic and/or ionogenic groups, and a total of 16 to 35% by weight of one or more sun protection filter substances, based on the total weight of the composition, to skin, wherein the at least one polyurethane urea is dispersed in water during or after step B, wherein the isocyanate-functional polyurethane prepolymers A) have a content of ionic and ionogenic groups below 1 milliequivalent per 100 g of polyurethane prepolymers, wherein at least one of said sun protection filter substances is octocrylene which is present in an amount of from 4 to 12% by weight, based on the total weight of the composition, and wherein the at least one polyurethane urea has repeat units containing urea groups, which are formed in the reaction of the isocyanate-functional prepolymers A) with the at least one amino-functional compound B), and wherein the sun protection composition has a SPF-boosting effect.

12. The cosmetic method as claimed in claim 11, wherein said composition, following application to the skin, at least partially remains on said skin.

13. The sun protection composition as claimed in claim 1, wherein said sun protection composition comprises a sun protection factor of at least 20 as measured in accordance with the SPF test method.

14. The sun protection composition as claimed in claim 1, wherein the at least one amino-functional compound B2) which comprises one or more ionic and/or ionogenic groups is 2-(2-aminoethylamino)ethanesulphonic acid and/or a salt thereof.

15. The sun protection composition as claimed in claim 6, wherein the at least one amino-functional compound B1) which comprises no ionic and/or ionogenic groups is a diamine which comprises no ionic and/or ionogenic groups.

16. The sun protection composition as claimed in claim 8, wherein said sulphonic acid and/or sulphonate group is a sodium sulphonate group.

17. The sun protection composition as claimed in claim 9, wherein said dibenzoyl methane derivative is 4-(t-butyl)-4'-methoxydibenzoylmethane.

18. The sun protection composition as claimed in claim 1, wherein said sun protection composition comprises 0.1 to 20% by weight of the at least one polyurethane urea based on the total weight of the composition.

19. The sun protection composition as claimed in claim 1, wherein said sun protection composition comprises octocrylene in an amount of from 8 to 11% by weight based on total weight of said sun protection composition.

* * * * *